United States Patent
Aoyama et al.

(10) Patent No.: US 6,291,728 B1
(45) Date of Patent: Sep. 18, 2001

(54) PROCESS FOR PRODUCING 1,1,1,3,3-PENTAFLUOROPROPANE

(75) Inventors: Hirokazu Aoyama; Tatsuo Nakada; Akinori Yamamoto, all of Settsu (JP)

(73) Assignee: Daikin Industries, Ltd., Osaka (JP)

( * ) Notice: Subject to any disclaimer, the term of this patent is extended or adjusted under 35 U.S.C. 154(b) by 0 days.

(21) Appl. No.: 09/043,130
(22) PCT Filed: Oct. 8, 1996
(86) PCT No.: PCT/JP96/02943
§ 371 Date: Mar. 27, 1998
§ 102(e) Date: Mar. 27, 1998
(87) PCT Pub. No.: WO97/13737
PCT Pub. Date: Apr. 17, 1997

(30) Foreign Application Priority Data

Oct. 13, 1995 (JP) .................................................. 7-291811

(51) Int. Cl.⁷ ...................................................... C07C 17/08
(52) U.S. Cl. ............................................................ 570/167
(58) Field of Search ............................................... 570/167

(56) References Cited

U.S. PATENT DOCUMENTS

| | | | |
|---|---|---|---|
| 3,806,589 | * 4/1974 | Becher et al. | 570/167 |
| 5,055,624 | * 10/1991 | Lantz et al. | 570/167 |
| 5,574,192 | * 11/1996 | VanDer Puy | 570/167 |

FOREIGN PATENT DOCUMENTS

| | | |
|---|---|---|
| 8-73385 | 3/1996 | (JP) . |
| 8-104655 | 4/1996 | (JP) . |
| 8-239334 | 9/1996 | (JP) . |

\* cited by examiner

*Primary Examiner*—Alan Siegel
(74) *Attorney, Agent, or Firm*—Armstrong, Westerman, Hattori, McLeland & Naughton LLP

(57) ABSTRACT

A manufacturing method for 1,1,1,3,3-pentafluoropropane, wherein 1,1,1,3,3-pentafluoropropane (HFC-245fa) is obtained by reacting halogenated propane, for example, 1,1,1,3,3-pentachloropropane and so on, which is represented by the general formula:

$$CX_3CH_2CHX_2$$

[In the general formula, X is fluorine atom (F) or chlorine atom (Cl), and all of X can not be fluorine atoms at the same time], with anhydrous hydrofluoric acid (HF) under the presence of antimony catalyst. HFC-245fa can be obtained with high yield and economical advantages through simple process.

5 Claims, No Drawings

PROCESS FOR PRODUCING 1,1,1,3,3-PENTAFLUOROPROPANE

This application is a 371 of PCT/JP96/02943 filed Oct. 8, 1996.

INDUSTRIAL FIELDS WHERE THE INVENTION CAN BE UTILIZED

This invention relates to a manufacturing method for 1,1,1,3,3-pentafluoropropane which is important for industrial applications as blowing agents, refrigerants and propellants which do not destroy ozone in the ozone layer.

PRIOR ART

As a manufacturing method for 1,1,1,3,3-pentafluoropropane (hereinafter, this can be called HFC-245fa), there have been known a method for producing HFC-245fa by a reduction reaction of 1,1,1,3,3-pentafluoro-3-hexachloropropane with hydrogen, which is produced by fluorinating 1,1,1,3,3,3-hexachloropropane obtained by addition reaction of carbon tetrachloride and vinylidene chloride (WO 95/04022), and a method for producing HFC-245fa by reduction reaction of 1,1,1,3,3-pentafluoro-2,3-dichloropropane or 1,1,1,3,3-pentafluoro-2,2,3-trichloropropane with hydrogen (EP 0611744).

However, either of the said methods for producing HFC-245fa requires two processing steps consisting of a fluorination step for chloride to produce a precursor and a reduction step for the produced compounds with hydrogen. This results in a long manufacturing process in industrial applications and inferior economics of scale.

OBJECT OF THE INVENTION

The object of the present invention is to provide a manufacturing method for producing HFC-245fa through simple process with high yield and economical advantages.

CONSTRUCTION OF THE INVENTION

As a result of eagerly studying the manufacturing methods for HFC-245fa so as to solve the above stated problems, the inventors found that HFC-245fa can be produced with high selectivity through a step of reacting 1,1,1,3,3-pentachloropropane (hereinafter, this can be called HCC-240fa) with anhydrous hydrofluoric acid (HF) under the presence of antimony catalyst, and that the products, which are not sufficiently fluorinated, for example, 1,1,1-trifluoro-3,3-dichloropropane, 1,1,1,3-tetrafluoro-3-chloropropane and so on, can also be led to HFC-245fa with high yield by again conducting the same step as that described above, thus enabling the production of HFC-245fa with economical advantages and with high yield by only fluorination step from a chloride as a starting material.

That is, this invention relates to a manufacturing method for 1,1,1,3,3-pentafluoropropane, wherein 1,1,1,3,3-pentafluoropropane (HFC-245fa) is obtained by reacting halogenated propane, which is represented by the general formula:

$$CX_3CH_2CHX_2$$

[In the general formula, X is fluorine atom (F) or chlorine atom (Cl), and all of X can not be fluorine atoms at the same time], with anhydrous hydrofluoric acid (HF) under the presence of antimony catalyst.

In the present invention, particularly, it is important that the reaction is conducted by using pentavalent antimony catalyst, trivalent antimony catalyst or the mixture of these two in liquid phase. As the antimony catalyst, fluorinated-chlorinated antimony which is obtained by fluorinating antimony pentachloride or antimony trichloride can be used as a catalyst. However, when some chlorine atoms are contained in the catalyst, chlorination of the starting material may occur to lower the selectivity of this reaction. Accordingly, it is preferable to use completely fluorinated antimony such as antimony pentafluoride or antimony trifluoride as the catalyst.

Antimony pentafluoride or antimony trifluoride can be used either alone or mixed each other for use. These catalysts can be reused for the reaction.

In the present invention, solvent is not specifically necessary, but anhydrous HF as a reaction material can be used as the solvent. Reaction solvent can be used if necessary, that is, it can be used as the solvent so long as it is inactive to the catalyst.

In the case of using antimony pentafluoride as the catalyst and anhydrous HF as the reaction solvent, the concentration of the antimony catalyst may be restricted according to the materials of the reaction container due to its strong corrosiveness. That is, when the reaction container is made of fluororesins, the concentration of the catalyst is not restricted in use, however, when the reaction container is made of anticorrosion substance such as Hastelloy C® (Haynes International, Inc.) and the like, the concentration of the catalyst is restricted. When antimony pentafluoride alone is used as the catalyst, the concentration is preferably not more than 1 mol % to the amount of anhydrous HF, and more preferably not more than 0.5 mol %, in view of the corrosion.

When the mixture of antimony pentafluoride and antimony trifluoride is applied, the mixing ratio of antimony pentafluoride to antimony trifluoride is preferably not more than 1 at molar ratio, more preferably not more than 0.5 at molar ratio, and the concentration of antimony pentafluoride in the mixture is preferably not more than 10 mol % to the amount of anhydrous HF, more preferably not more than 3 mol %, in view of the corrosion.

When antimony trifluoride alone is used as the catalyst and anhydrous HF is used as the reaction solvent, the concentration of the catalyst would not be restricted because the corrosiveness is very small.

Reaction temperature may not specifically be limited, but 50° C. to 200° C. is preferable, 60° C. to 180° C. is more preferable.

Also, reaction pressure may not specifically be limited, but a range from atmospheric pressure to 50 kg/cm²G, more preferably from atmospheric pressure to 30 kg/cm²G, can be applied.

The molar ratio of the starting material and anhydrous HF can be optionally varied. But, practically, an amount of HF is preferably not less than the stoichiometric amount needed for converting the starting material to HFC-245fa. It can preferably be used in an amount of not less than 5 times the stoichiometric amount, or not less than 100 times the stoichiometric amount as occasion demands.

Reaction products obtained in the reaction of the present invention are varied with the reaction conditions. Fluorotetrachloropropane (HCFC-241, including isomer), difluorotrichloropropane (HCFC-242, including isomer), trifluorodichloropropane (HCFC-243, including isomer), tetrafluorochloropropane (HCFC-244, including isomer) and so on, which are insufficiently fluorinated products, can be obtained besides HFC-245fa. These insufficiently fluorinated materials can be effectively used by being recycled to the fluorination reactor after separation from the produced reaction mixture.

A method for recycling also can be applied wherein HFC-245fa as the final objective, hydrofluoric acid and HCl as by-product of the reaction should be separated from the system of reaction by the fractional distillation tower attached to the fluorination reaction apparatus, and the insufficiently fluorinated materials having higher boiling point among the above products should be directly returned to the reactor.

1,1,1,3,3-pentachloropropane, which can be used as a starting material in the present invention, can be easily obtained by addition reaction of carbon tetrachloride and vinyl chloride (Journal of Molecular Catalysis, Vol.77, 51 page, 1992, and Journal of Chemical Technology, Vol.72, No.7, 1526 page, 1969).

As the reaction systems of the present invention, there can be applied a batch system wherein the reaction is conducted after supplying necessary starting materials so as to recover the products and so on, a semi-batch system wherein the products and so on are taken out continuously while one of the starting materials is supplied continuously, and a continuous system wherein the products and so on are taken out continuously while the starting materials are supplied continuously.

Possibility of Utilizing the Invention in Industry

According to the method of the present invention, HFC-245fa can be obtained with high selectivity by reacting 1,1,1,3,3-pentahalopropane such as 1,1,1,3,3-pentachloropropane with anhydrous HF under the presence of antimony catalyst, and insufficiently fluorinated products, for example, 1,1,1-trifluoro-3,3-dichloropropane and 1,1,1,3-tetrafluoro-3-chloropropane can also be led to HFC-245fa with high yield by again conducting the same step as that described above. Accordingly, a manufacturing method for HFC-245fa having economical superiority, wherein it can be produced with high yield by only fluorination step of halogenated propane, can be provided.

Embodiments

The present invention will be explained more concretely in the following examples.

EXAMPLE 1

2.0 g of $SbF_5$ was charged into a Hastelloy made autoclave having a 200 mL internal volume. Then, after the autoclave was cooled to −30° C., 50 g of anhydrous HF and 22 g of 1,1,1,3,3-pentachloropropane were added. It was heated with stirring until the inside temperature reached 80° C.

Because the internal pressure went up by produced HCl, the producer gas was taken outside the reaction system through a water-washing tower, a calcium chloride tower and a cold trap at −70° C. to set the reaction pressure at 10 kg/cm²G. After the reaction was continued for 8 hours at 80° C., as keeping inner temperature at 50° C., the reaction mixture from the autoclave was collected in the same cold trap as mentioned above while HF was removed by a water-scrubber and an alkaline solution scrubber.

The amount of organic compounds collected in the cold trap was 7.5 g, and these were analyzed by gas chromatography. As a result of analysis, it was found that HFC-245fa was 52%, HCFC-244 (including isomer) was 24%, HCFC-243 (including isomer) was 19% and HCFC-242 (including isomer) was 1%.

EXAMPLE 2

From Example 1, 4.0 g of $SbF_5$, 95 g of anhydrous HF, and furthermore 40 g of a mixture of HCFC-244 (including isomer) and HCFC-243 (including isomer) [HCFC-244:HCFC-243=56:44] were added in the same reactor. Then, as the reaction temperature and the reaction pressure were kept at 90° C. and 12 kg/cm²G respectively, the reaction was conducted for 5 hours in the same way as described above. A result of the same analysis showed that HFC-245fa was 95%, HCFC-244 (including isomer) was 3% and HCFC-243 (including isomer) was 2%.

EXAMPLE 3

5.4 g of $SbF_5$ and 8.9 g of $SbF_3$ in place of $SbF_5$ were added and reacted in the same way as Example 1. A result of the same analysis showed that HFC-245fa was 50%, HCFC-244 (including isomer) was 25%, HCFC-243 (including isomer) was 20% and HCFC-242 (including isomer) was 1%.

EXAMPLE 4

7.7 g of $SbF_5$ was charged into SUS316 made autoclave with a 200 mL internal volume of inner tube made of PTFE (polytetrafluoroethylene). Then, after the autoclave was cooled to −30° C., 42 g of anhydrous HF and 22 g of 1,1,1,3,3-pentachloropropane were added. It was heated with stirring until the inside temperature reached 80° C.

Because the internal pressure went up by produced HCl, the produced gas was taken outside the reaction system through a water-washing tower, a calcium chloride tower and a cold trap at −70° C. to set the reaction pressure being 13 kg/cm²G. After the reaction was continued for 5 hours at 80° C., as keeping inner temperature at 50° C., the reaction mixture from the autoclave was collected in the same cold trap as mentioned above while HF was removed by a water-scrubber and an alkaline-solution. scrubber.

The amount of organic compounds collected in the cold trap was 6.8 g, and these were analyzed by gas chromatography. As a result of analysis, it was found that HFC-245fa was 54%, HCFC-244 (including isomer) was 22%, HCFC-243 (including isomer) was 18% and HCFC-242 (including isomer) was 0.5%.

And, after 42 g of anhydrous HF and 22 g of 1,1,1,3,3-pentachloropropane were charged again into the reactor wherein the catalyst was remained, the reaction was conducted in the same way as described above to recover reaction products. The amount of organic compounds was 8.8 g, and a result of analysis by gas chromatography showed that HFC-245fa was 53%, HCFC-244 (including isomer) was 23%, HCFC-243 (including isomer) was 18% and HCFC-242 (including isomer) was 1%.

What is claimed is:

1. A manufacturing method for 1,1,1,3,3-pentafluoropropane, wherein 1,1,1,3,3-pentafluoropropane is obtained by reacting halogenated propane, which is represented by the general formula:

$CX_3CH_2CHX_2$ wherein, in the general formula, X is fluorine atom or chlorine atom, and all of X can not be fluorine atoms at the same time, with anhydrous hydrofluoric acid under the presence of antimony catalyst consisting of pentavalent antimony, or a mixture of pentavalent antimony and trivalent antimony where antimony pentafluoride is used in a concentration of not more than 10 mol % to the amount of anhydrous hydrofluoric acid, wherein the pentavalent antimony, when used alone, being in a concentration of not more than 1 mol % to the amount of the anhydrous hydrofluoric acid, and wherein, when the mixture of pentavalent antimony and trivalent antimony is used and the concentration of antimony pentafluoride is from 1 to 10 mol % to the amount of anhydrous hydrofluoric acid, the ratio of antimony pentafluoride to antimony trifluoride is not more than 1 at molar ratio.

2. A manufacturing method as defined by claim 1, wherein a mixture of antimony pentafluoride and antimony trifluoride is used as the antimony catalyst.

3. A manufacturing method as defined by claim 1, wherein antimony pentafluoride is used as the antimony catalyst.

4. A manufacturing method as defined by claim 1, wherein the reaction is conducted in liquid phase.

5. A manufacturing method as defined by claim 1, wherein the reaction is conducted in anhydrous hydrofluoric acid as solvent.

* * * * *